(12) United States Patent
Borsoi et al.

(10) Patent No.: US 10,386,221 B2
(45) Date of Patent: Aug. 20, 2019

(54) METHOD FOR DETERMINING THE FILL STATE IN A TANK UTILIZING ULTRASONIC WAVES AND REFERENCE SURFACES

(71) Applicant: CONTINENTAL AUTOMOTIVE GMBH, Hannover (DE)

(72) Inventors: Sonny Borsoi, Thionville (FR); Cheikh Diouf, Silly-sur-Nied (FR); Mathieu Dupriez, Les Étangs (FR); Denis Mesmer, Bouzonville (FR)

(73) Assignee: Continental Automotive GmbH, Hannover (DE)

( * ) Notice: Subject to any disclaimer, the term of this patent is extended or adjusted under 35 U.S.C. 154(b) by 105 days.

(21) Appl. No.: 15/405,897

(22) Filed: Jan. 13, 2017

(65) Prior Publication Data

US 2017/0122789 A1    May 4, 2017

Related U.S. Application Data

(63) Continuation of application No. PCT/EP2015/065942, filed on Jul. 13, 2015.

(30) Foreign Application Priority Data

Jul. 14, 2014 (DE) .................. 10 2014 109 843

(51) Int. Cl.
*F01N 3/20* (2006.01)
*G01F 23/00* (2006.01)
(Continued)

(52) U.S. Cl.
CPC ....... *G01F 23/2962* (2013.01); *F01N 3/2066* (2013.01); *G01F 23/0061* (2013.01);
(Continued)

(58) Field of Classification Search
CPC ............. G01F 23/2962; G01F 23/2968; G01F 25/0061; G01F 23/296; G01F 23/2961;
(Continued)

(56) References Cited

U.S. PATENT DOCUMENTS 2,869,108 A * 1/1959 Smith, Jr. ............... G01S 7/003
114/126
3,214,974 A * 11/1965 Altman .................. G01F 23/296
367/151
(Continued)

FOREIGN PATENT DOCUMENTS

DE    4307635 A1    12/1899
DE    4025326 A1 *  11/1991 ......... G01F 23/2962
(Continued)

OTHER PUBLICATIONS

Translation of International Search Report and Written opinion dated Jan. 14, 2017 from corresponding International Patent Application No. PCT/EP2015/065942 (Year: 2017).*
(Continued)

*Primary Examiner* — Daniel S Larkin
*Assistant Examiner* — David L Singer (57) ABSTRACT

The disclosure relates to a method for determining a level of a liquid in a tank with an ultrasonic fill state sensor and at least two reference surfaces for reflecting an ultrasonic wave transmitted by the ultrasonic fill state sensor. A first reference surface is arranged below a second reference surface. The method includes determining a first propagation speed of an ultrasonic wave to the first reference surface on a first measurement path and a second propagation speed from the first reference surface to the second reference surface on a second measurement path. The method also includes measuring a propagation time of an ultrasonic wave from the ultrasonic fill state sensor to a liquid level of the liquid in the tank, selecting the first propagation speed or the second
(Continued)

propagation speed based on at least one selection criterion, and calculating a fill state using the propagation time measured.

20 Claims, 6 Drawing Sheets

(51) Int. Cl.
  *G01F 25/00* (2006.01)
  *G01F 23/296* (2006.01)
  *G01N 29/024* (2006.01)

(52) U.S. Cl.
  CPC ....... *G01F 25/0061* (2013.01); *G01N 29/024* (2013.01); *F01N 2610/02* (2013.01); *F01N 2610/1406* (2013.01); *F01N 2900/1814* (2013.01); *G01N 2291/011* (2013.01); *G01N 2291/0222* (2013.01); *G01N 2291/02836* (2013.01); *G01N 2291/045* (2013.01); *G01N 2291/101* (2013.01); *Y02A 50/2325* (2018.01); *Y02T 10/24* (2013.01); *Y10S 367/902* (2013.01); *Y10S 367/908* (2013.01)

(58) Field of Classification Search
  CPC .................. G01F 23/28; G01F 23/284; G01F 23/282–23/2928; Y10S 367/908; G01N 2291/045; G01S 2007/52014; F01N 2560/12; F01N 2610/148; F01N 2900/1814
  USPC ........... 73/292, 290 V, 61.49, 152.51, 290 R, 73/291, 597; 181/124; 367/99, 100, 908, 367/151; 702/55, 159; 340/621; 220/4.14
  See application file for complete search history.

(56) References Cited

U.S. PATENT DOCUMENTS

| | | | | | |
|---|---|---|---|---|---|
| 3,290,944 | A | * | 12/1966 | Altman | G01K 11/26 374/201 |
| 4,320,659 | A | * | 3/1982 | Lynnworth | G01F 1/66 73/290 V |
| 4,748,846 | A | * | 6/1988 | Haynes | G01F 23/2962 73/290 V |
| 4,805,453 | A | * | 2/1989 | Haynes | G01F 23/2961 367/908 |
| 5,036,703 | A | * | 8/1991 | Eriksson | G01F 23/2962 181/124 |
| 5,095,748 | A | * | 3/1992 | Gregory | G01F 23/2961 702/54 |
| 5,121,340 | A | * | 6/1992 | Campbell | G01F 23/2962 181/124 |
| 5,127,266 | A | * | 7/1992 | Maresca | G01F 23/2962 181/124 |
| 5,226,320 | A | * | 7/1993 | Dages | G01F 23/2962 181/124 |
| 5,228,339 | A | * | 7/1993 | Maresca, Jr. | G01F 23/28 367/908 |
| 5,263,371 | A | * | 11/1993 | Maresca, Jr. | G01F 23/2962 181/124 |
| 5,301,549 | A | * | 4/1994 | Sinclair | G01F 23/2961 340/621 |
| 5,309,763 | A | * | 5/1994 | Sinclair | G01F 23/2961 181/124 |
| 5,357,801 | A | * | 10/1994 | Sinclair | G01F 23/2962 181/124 |
| 5,568,449 | A | * | 10/1996 | Rountree | G01F 23/2962 367/902 |
| 5,670,710 | A | * | 9/1997 | Atkinson | G01F 23/2962 73/290 V |
| 5,765,433 | A | * | 6/1998 | Johnson | G01F 17/00 73/290 V |
| 5,856,953 | A | * | 1/1999 | Durkee | G01F 23/2962 367/908 |
| 6,202,484 | B1 | * | 3/2001 | Willner | G01F 23/2962 73/290 V |
| 6,435,024 | B1 | * | 8/2002 | Alvarez | G01F 23/2961 73/290 V |
| 6,684,919 | B2 | * | 2/2004 | Gaiser | G01F 23/284 141/198 |
| 8,919,370 | B2 | | 12/2014 | Krause et al. | |
| 9,897,477 | B2 | * | 2/2018 | Maguin | F01N 3/2066 |
| 2004/0007061 | A1 | * | 1/2004 | Forgue | G01F 23/2962 73/290 V |
| 2009/0282911 | A1 | * | 11/2009 | Bostrom | G01F 23/2962 73/290 V |
| 2010/0018309 | A1 | * | 1/2010 | Marcovecchio | G01F 23/2962 73/290 V |
| 2010/0242593 | A1 | * | 9/2010 | Lagergren | G01D 5/48 73/290 V |
| 2013/0118252 | A1 | * | 5/2013 | Hartmann | G01F 23/296 73/290 V |
| 2015/0000396 | A1 | * | 1/2015 | Maguin | F01N 3/2066 73/290 V |
| 2015/0019108 | A1 | * | 1/2015 | Hendrickson | F01N 11/00 701/102 |
| 2015/0323373 | A1 | * | 11/2015 | Maguin | G01N 29/024 73/290 V |

FOREIGN PATENT DOCUMENTS

| | | | | |
|---|---|---|---|---|
| DE | 19710599 A1 | * | 10/1997 | ........ G01F 23/2962 |
| DE | 102004028547 A1 | * | 2/2006 | ........ G01F 23/2962 |
| DE | 102012207724 A1 | | 11/2013 | |
| DE | 102012207732 A1 | | 11/2013 | |
| RU | 2502612 C2 | | 12/2013 | |
| WO | WO2007014721 A1 | | 2/2007 | |
| WO | WO 2013135486 A1 | * | 9/2013 | .......... F01N 3/2066 |
| WO | WO2013135486 A1 | | 9/2013 | |
| WO | WO 2014090848 A1 | * | 6/2014 | .......... G01N 29/024 |
| WO | WO2014090848 A1 | | 6/2014 | |

OTHER PUBLICATIONS

Machine Translation of German Search Report dated May 3, 2015 for corresponding German Patent Application No. 10 2014 109 843.9 (Year: 2015).*

German Search Report dated May 3, 2015 for corresponding German Patent Application No. 10 2014 109 843.9.

* cited by examiner

METHOD FOR DETERMINING THE FILL STATE IN A TANK UTILIZING ULTRASONIC WAVES AND REFERENCE SURFACES

CROSS-REFERENCE TO RELATED APPLICATIONS

This application claims the benefit of PCT Application PCT/EP2015/065942, filed Jul. 13, 2015, which claims priority to German Application DE 10 2014 109 843.9, filed Jul. 14, 2014. The disclosures of the above applications are incorporated herein by reference.

TECHNICAL FIELD

The disclosure relates to a method for determining the level in a tank for a liquid. The method may be used for determining the level in a tank in a motor vehicle, in which a liquid additive for exhaust gas cleaning is stored.

BACKGROUND

Motor vehicles with exhaust treatment devices, in which a liquid additive for exhaust gas cleaning is added, are widely used. Exhaust treatment devices in which the method of selective catalytic reduction (SCR method, SCR=Selective Catalytic Reduction) is performed are encountered particularly frequently. With this method, nitrogen oxide compounds in the exhaust gas with ammonia are reduced to harmless substances such as nitrogen, water and $CO_2$. Ammonia is not normally stored directly in a motor vehicle, but in the form of a liquid additive, which can be stored in a tank. Such a liquid additive for exhaust gas cleaning is then converted to ammonia outside the exhaust gas in a reactor provided for the purpose or within the exhaust gas in an exhaust treatment device. Particularly frequently, a urea-water solution is used as the liquid additive. A urea-water solution with a urea content of 32.5% by weight is available under the trade name AdBlue®.

It is frequently necessary to obtain information about the level in a tank for liquid additive. Information about the level can be used to determine suitable points in time for filling the tank. Moreover, it can be prevented that the tank is completely emptied during operation.

Ultrasonic level sensors have already been proposed for determining the level in a tank for liquid additive. Ultrasonic level sensors normally include an ultrasonic transmission unit and an ultrasonic receiving unit. The ultrasonic transmission unit transmits an ultrasonic wave, which is reflected at a liquid surface within the tank and from there returns to the ultrasonic level sensor and is received by the ultrasonic receiving unit of the ultrasonic level sensor. The propagation speed of the ultrasonic wave in the liquid in the tank is either known or it is determined with a reference measurement. The level in the tank is computed from the propagation time of the ultrasonic wave from the ultrasonic level sensor to the liquid level and back to the ultrasonic level sensor and the propagation speed of the ultrasonic wave in the liquid.

An advantage of ultrasonic level sensors is that they do not include any movable parts. Moreover, with ultrasonic level sensors it is possible to measure the level in a tank with the same sensor design even for different tank heights. Differences with regard to the possible level in the tank only have to be stored in an evaluation unit with which the ultrasonic waves received by the ultrasonic receiving unit are evaluated. Ultrasonic waves received by the ultrasonic receiving unit, which originate from the ultrasonic waves emitted by the ultrasonic transmission unit and were, for example, reflected at the liquid surface, are also referred to below as signals or as response signals, which are received by the ultrasonic receiving unit or by the ultrasonic level sensor.

Two different arrangements of ultrasonic level sensors in a tank are known. According to a known arrangement, ultrasonic waves are sent from an upper point to a liquid level in the tank and are reflected from there back up to the ultrasonic level sensor. In another known arrangement, ultrasonic waves are sent from an ultrasonic level sensor on the floor of the tank through the liquid to the liquid level in the tank, and are reflected at the liquid level back to the ultrasonic level sensor on the floor of the tank.

It has already been explained above that a reference measurement can be performed for determining the propagation speed of ultrasonic waves in a liquid. It is known to determine the propagation time of an ultrasonic wave along a known measuring distance in the liquid for the reference measurement. A measuring distance can be implemented, for example, with at least one reference surface at which the ultrasonic wave is reflected. Preferably, the position of the reference surface or the distance between two reference surfaces is accurately known. A speed of travel of the ultrasonic wave in the liquid is determined using the propagation time of the ultrasonic wave to the reference surface or using a difference of the propagation times of the ultrasonic waves to a plurality of (e.g. two) reference surfaces.

In carrying out such a reference measurement it is problematic that the measuring distance given by the at least one reference surface must be disposed fully within the liquid. This is especially problematic with changing levels and fill heights of the liquid in the tank. It is therefore known to arrange the reference surfaces such that the measuring distance for determining the speed of travel in the ultrasonic wave is horizontal, preferably close to the bottom of the tank. This enables it to be guaranteed that a propagation time measurement can be performed even for very low levels. It is a disadvantage that the horizontal arrangement of a measuring distance takes up a relatively large installation space at the bottom of the tank.

SUMMARY

It is therefore an object of the present disclosure to solve or at least to alleviate the described technical problems. In particular, a particularly advantageous method for determining the level in a tank for a liquid with an ultrasonic sensor is to be presented.

One aspect of the disclosure relates to a method for determining the level in a tank with an ultrasonic level sensor and at least two reference surfaces for reflection of an ultrasonic wave that is emitted by the ultrasonic level sensor, where a first reference surface is disposed below a second reference surface. The method includes the following steps: a) determining a first propagation speed of an ultrasonic wave in the liquid over a first measuring distance from the ultrasonic level sensor to the first reference surface; and b) determining a second propagation speed of an ultrasonic wave in the liquid over a second measuring distance from the first reference surface to the second reference surface. The method also includes the following steps: c) measuring a propagation time of an ultrasonic wave from the ultrasonic level sensor to a liquid level of the liquid in the tank; d) selecting the first propagation speed or the second propagation speed depending on at least one selection criterion; and e) computing a level with the propagation time measured in step c) and the propagation speed selected in step d).

Implementations of the disclosure may include one or more of the following optional features. In some implementations, the ultrasonic sensor is disposed in the bottom of the tank or close to the bottom of the tank. The ultrasonic level sensor may be oriented vertically upwards, so that ultrasonic waves are sent vertically upwards from the ultrasonic level sensor. The first reference surface and the second reference surface may be disposed vertically above the ultrasonic level sensor. In some example, the ultrasonic level sensor may include a transmitter unit for emitting ultrasonic waves and a receiver unit for receiving ultrasonic waves, where the receiver unit is designed to receive ultrasonic waves that have been emitted by the transmitter unit and reflected at any structure (reference surfaces, liquid level in the tank etc.).

In some implementations, the steps a), b) and c) of the method are at least partly carried out together (simultaneously). In some examples, the ultrasonic level sensor transmits a signal in the form of an ultrasonic wave. The ultrasonic level sensor then receives three reflected response signals that arise from the transmitted ultrasonic wave. The first signal is identified as the reflection at the first reference surface. Step a) is carried out with the signal. The length of the first measuring distance is known and the first propagation speed can be computed from the time interval between the emission of the ultrasonic wave and the reception of the first response signal. The second response signal is identified as the reflection of the ultrasonic wave at the second reference surface. The first response signal and the second response signal are used for determining the second propagation speed in step b). The second propagation speed can be computed from the difference between the point in time of the reception of the first response signal and the point in time of the reception of the second response signal and the (known) length of the second measuring distance. In some examples, the third response signal is used to carry out step c) and to determine the propagation time of the ultrasonic wave from the level sensor to a liquid level of the liquid in the tank. The propagation time may be derived from the time interval between transmitting the ultrasonic wave and receiving the third response signal.

Steps a), b) and c) may also be carried out differently (together or in a different order). The explanation of steps a), b) and c) described here is to be understood as only exemplary.

In some examples, by the selection of the first propagation speed or the second propagation speed depending on at least one selection criterion in step d), it is possible to determine the (current) level in the tank even if the second (upper) reference surface is not disposed within the liquid in the tank, but the liquid level in the tank is positioned between the first reference surface and the second reference surface. In particular, the selection criteria may be defined such that a level can be determined with the first propagation speed if the liquid level in the tank is below the second reference surface. For higher levels (above the second reference surface), the second propagation speed is selected for determining the level. The second propagation speed has the advantage relative to the first propagation speed that it can be determined considerably more accurately. This is because the distance between the first reference surface and the second reference surface is specified significantly more accurately than the distance between the ultrasonic level sensor and the first reference surface. This is especially due to the fact that the first reference surface and the second reference surface are disposed on a (common) calibration component. In contrast, the ultrasonic sensor is a (separate) component from the reference surfaces, so that tolerances of the distance between the ultrasonic level sensor and the first reference surface are less accurate than tolerances of the distance between the two reference surfaces. The first propagation speed has the advantage compared to the second propagation speed that this can also be determined for levels below the second reference surface.

The described method enables even low levels in a tank to be reliably determined and to simultaneously guarantee a vertical arrangement of the ultrasonic level sensor in the tank. This significantly reduces the space requirement of the level sensor at the bottom of the tank. For example, the vertically arranged ultrasonic level sensor with the reference surfaces can be mounted in a small opening in a floor of the tank. In contrast, an ultrasonic level sensor with horizontally arranged reference surfaces needs a complex fitting and/or an opening in the bottom of the tank whose diameter is at least as large as the length of the measuring distance.

The method is particularly advantageous if the ultrasonic level sensor is disposed outside of the tank and an ultrasonic wave of the ultrasonic level sensor passes through a coupling layer before it enters the liquid in the tank, where the coupling layer includes a tank wall (especially a segment of the tank wall) and the propagation time of the ultrasonic wave in the coupling layer is taken into account with a correction factor in step a).

In some examples, the ultrasonic level sensor is disposed outside a tank interior on a side of a tank wall opposite from the liquid. The coupling layer may include a transmission means in addition to the tank wall that couples the ultrasonic level sensor to the tank wall so as to conduct ultrasound. In some examples, the transmission means includes a conductive paste or a conductive pad, which is disposed between the tank wall and the ultrasonic sensor. The ultrasonic waves normally have a different propagation speed within the coupling layer than in the liquid in the tank. Because the design of the coupling layer is known, the speed of the ultrasonic waves in the coupling layer may be computed and taken into account in step a) as a correction factor. In some examples, the correction factor has the dimension of a time. In some examples, the time needed by the ultrasonic waves to pass through the coupling layer is determined by experiment and stored in the form of the correction factor in a controller for carrying out the described method.

The method is also advantageous if which propagation speed was selected for a preceding iteration of the method is taken into account when selecting the propagation speed in step d).

The described method is normally repeated iteratively (during the operation of a motor vehicle), in order to always be able to provide current information about the level of the liquid in the tank. The parameters used and determined in the method (especially the selected propagation speed) are each stored in a controller of the motor vehicle. It is therefore possible to access parameters during an iteration of the method that were determined during a previous iteration of the method. The information about the selected propagation speed during a previous iteration of the method may be used in step c) in addition to the at least one selection criterion in order to select one of the propagation speeds. For example, the option of a change of the selected propagation speed in step d) can be deactivated if certain conditions exist. A change of the selected propagation speed means here that when carrying out the method a different (first or second) propagation speed is selected than for a previous iteration of the method. For example, in principle a change from the selection of the first propagation speed (back) to the selection of the second propagation speed can be prevented. This means that for a single selection of the first propagation speed, a step back of the method to the first propagation speed in a subsequent iteration of the method is not possible. If additional conditions are fulfilled, the change (back) to the selection of the second propagation speed can be enabled again.

In some Implementations, it is conceivable that in step d) the first propagation speed is selected, because the at least one selection criterion allows it to be identified that the level in the tank has fallen below the second reference surface. If this is the case for the first time, the selection of the first propagation speed is stored in a memory. In some examples, the first propagation speed remains selected while no refilling of the tank is carried out. Even if the at least one selection criterion would actually specify a change back to the second propagation speed, the first propagation speed remains selected.

Furthermore, the method is advantageous if a computed level is used as the first selection criterion in step e), where for a level below a level limit value, the first propagation speed is selected and for a level above a level limit value, the second propagation speed is selected.

In some implementations, the level limit value is arranged so that for levels above the level limit value both reference surfaces are disposed (reliably) within the liquid, so that determining the second propagation speed over the second measuring distance between the two reference surfaces is possible without problems. The level limit value is accordingly preferably specified at the height of the second reference surface, or slightly above the second reference surface. For levels below the level limit value, the computation of the level preferably takes place with the second propagation speed, so that the further reduction of the level does not affect the level determination.

Furthermore, the method is advantageous if in step d) a comparison between the first propagation speed and the second propagation speed is performed as the second selection criterion, where the first propagation speed is selected if a speed deviation between the first propagation speed and the second propagation speed exceeds a limit value.

It was described above that the first propagation speed, the second propagation speed, and the propagation time are each determined using three response signals, which arrive successively at a receiver unit of the ultrasonic level sensor in response to an emitted ultrasonic wave. If the liquid level reduces below the second reference surface, no more ultrasonic waves are reflected at the second reference surface, because all ultrasonic waves are already reflected at the liquid level. The second reference surface is thus not visible to the ultrasonic level sensor. Instead, the liquid level is considered to be the second reference surface because this produces the second response signal to the emitted ultrasonic wave after the first reference surface. For levels below the second reference surface, the propagation time determined with the level sensor between a response signal that corresponds to the first reference surface and the second response signal that is interpreted by the ultrasonic sensor as belonging to the second reference surface reduces accordingly. As a result of this, for levels below the second reference surface deviations occur between the second propagation speed determined in step b) and the first propagation speed determined in step a). Because of inaccuracies of the speed measurements in steps a) and b), speed deviations occur between the two propagation speeds even for levels above the second reference surface. The speed differences are, however, relatively small. In some examples, the speed limit is defined such that only speed differences are recorded that are caused by a reduction of the level below the second reference surface.

If the liquid level has reduced to below the second reference surface, an adapted procedure for step c) is normally also necessary. In particular, it is no longer possible to use a third response signal to an emitted ultrasonic wave for determining the propagation time. Rather, a second response signal should be used for determining the propagation time to the liquid level, because the reflection of the ultrasonic wave at the liquid level is typically received as the second response signal by the ultrasonic level sensor if the liquid level is below the second reference surface.

In some implementations, the first selection criterion and the second selection criterion are both used to change from the first propagation speed to the second propagation speed. In some examples, both selection criteria must specify a corresponding change of propagation speed so that this change also actually takes place in step d).

For a change from the first propagation speed (back) to the second propagation speed, it may be necessary that additionally, another (third) selection criterion, which is explained below, specifies a corresponding change.

In some example, the method is advantageous if the propagation time measured in step c) is checked as the third selection criterion in step d), where the second propagation speed is not selected if the measured propagation time is outside a time interval that corresponds to twice the propagation time to the second reference surface and the first propagation speed was selected for a previous iteration of the method.

It was described above that three response signals to an ultrasonic wave emitted by the ultrasonic level sensor can be used for determining the first propagation speed, the second propagation speed and the propagation time respectively. In connection with the second selection criterion, it was explained that the second reference surface may not be visible for the ultrasonic sensor if the liquid level is below the second reference surface, because in this case the liquid level produces the second response signal and fully reflects the ultrasonic waves. Nevertheless, in this case there is also a third response signal, which can erroneously be interpreted as the liquid level. The third response signal arises as a result of multiple reflections of the ultrasonic wave within the tank. It has been found that a particularly strong response signal is produced by an ultrasonic wave that is first reflected at the liquid level, then at the bottom of the tank and then again at the liquid level, before it passes back to the ultrasonic level sensor. The ultrasonic wave of the third response signal thus traverses the path from the ultrasonic level sensor to the liquid level exactly four times instead of exactly twice. As a result of this, the propagation time gives exactly twice the propagation time of the second response signal (from the second reference surface). The time interval is defined such that it identifies propagation times to the liquid level or the third response signals, which correspond to twice the propagation time to the second reference surface. The time interval preferably covers twice the propagation time mentioned with a tolerance of between 5% and 10%, so that measurement inaccuracies are also detected. If a level were to be computed based on the second propagation speed, and simultaneously the third response signal were to be erroneously interpreted as the propagation time to the liquid level, step e) would give a computed level that would correspond to twice the actual level in the tank. To reliably avoid the erroneous result of the method, the third selection criterion intercepts corresponding cases.

In some examples, the third selection criterion is only used for a change from the first propagation speed to the second propagation speed. The third selection criterion can thus also be referred to as an additional control criterion.

In addition, the method is advantageous if, during the calculation of the level in step e), the following substeps are executed: i) computing the level based on the selected propagation speed; ii) checking whether a level which is determined at the second propagation speed corresponds to twice the height of the second reference surface; and iii) determining a fluctuation in a second response signal of the second reference surface at the ultrasonic level sensor in a time interval. During the calculation of the level in step e) the following substeps are also executed: iv) checking whether the fluctuation in the second response signal exceeds a prespecified limit value; and v) correcting the level which is computed in step i) to the height of the second reference surface (2) when steps ii) and iv) are complete.

In some examples, the second response signal, which is used in step iii), at the ultrasonic level sensor is preferably intended to be associated with the second reference surface, while a first response signal is intended to be associated with the first reference surface, and a third response signal is intended to be associated with the liquid level in the tank.

As already explained above, the third response signal may, however, correspond to twice the reflection of the ultrasonic waves at the liquid level if the liquid level or the level is at the height of the second reference surface. The possibility of this situation being present is identified in substep ii). However, this situation cannot be distinguished from the situation of the filling level actually lying at twice the height of the second reference surface on the basis of substep ii). This is possible using substeps iii) and iv). Fluctuations in the second response signal in substep iii) are triggered by vibrations and/or sloshing movements of the liquid in the tank if the level is at the height of the second reference surface. This is because the second reference surface is then at least also briefly above the liquid level in the event of sloshing movements, and the liquid level therefore causes the second response signal. This cannot occur if the level corresponds to twice the height of the second reference surface. In this case, the second reference surface is always and reliably completely covered by liquid and the second response signal is accordingly constant. It is therefore possible to draw a distinction between whether the filling level actually corresponds to twice the height of the second reference surface or whether the ultrasonic wave is reflected twice at the liquid surface (substeps iii) and iv)) by observing the fluctuation in the second response signal in a time interval and by comparing the observed fluctuation (which may be averaged over time).

Furthermore, the method is advantageous if in step d) a change from the first propagation speed to the second propagation speed only takes place if a stationary mode exists.

A stationary mode is characterized in that a motor vehicle in which the method is being performed was or is deactivated (in the meantime). The opposite of the stationary mode is a dynamic mode, in which the motor vehicle was or is (continuously) activated. The distinction between a stationary mode and a dynamic mode can take place in a mode check. If a stationary mode exists, it is possible that the tank was refilled, because refilling the tank normally requires the motor vehicle (at least briefly) to be deactivated or stopped. If the stationary mode exists, it is also possible (in principle) that the liquid level in the tank has risen. Accordingly, a change back to the second propagation speed is (preferably) only possible if a stationary mode exists or at least has existed. In a dynamic mode during the operation of a motor vehicle, it is assumed that an increase of the liquid level to a value above the second reference surface was caused by sloshing of the liquid in the tank, by an inclined position of the tank or similar. Accordingly, a change back to the second propagation speed is then not useful.

Drawing a distinction between a static mode and a dynamic mode is useful, in particular, in connection with substeps i) to v) of step e). Fluctuations which can be evaluated within the scope of substeps iii) and iv) occur regularly only in the dynamic mode because sufficient sloshing movements and/or vibrations of the liquid level which are required to create a difference between levels at the height of the second reference surface and at twice the height of the second reference surface do not occur in the static mode. Therefore, substeps i) to v) may be employed only in the dynamic mode and have to be adapted for a static mode. In some examples, level information that is stored in a memory may be used in the static mode in this case.

Furthermore, the method is advantageous if an input signal of the at least one selection criterion used in step d) is filtered with a low pass filter.

An input signal of the at least one selection criterion is, for example, a level computed in step e) for the first selection criterion and for the third selection criterion or a speed deviation for the second selection criterion. The input signal to be filtered can, for example, also be a propagation time of the ultrasonic wave. A low pass filter has the properties that short-term fluctuating changes of the selection criterion are filtered out. Using a low pass filter it can, for example, be prevented that sloshing movements of the liquid in the tank affect the at least one selection criterion.

In some implementations, the method is advantageous if an input signal of the at least one selection criterion used in step d) is filtered with a hysteresis.

By filtering an input signal with a hysteresis, rapid changes of the selected propagation speed can be effectively prevented.

A motor vehicle with a tank for an operating liquid includes an ultrasonic level sensor for determining the level in the tank and at least two reference surfaces for reflection of an ultrasonic wave emitted by the ultrasonic level sensor, where a first reference surface is disposed below a second reference surface, and with at least one controller that is arranged for level determination for implementing the described method, will also be described here.

The particular advantages, implementations, and examples described in connection with the described method can be transferred in an analogous manner to the motor vehicle and the ultrasonic level sensor (as a device).

The controller can be a controller associated with the ultrasonic level sensor in a device for delivery and provision of liquid additive. The controller can also be a component of a motor vehicle controller in which software for performing the described method is stored.

The disclosure and the technical environment are described in detail below using the figures. The figures show examples, to which the disclosure is not limited, however. In particular, it is to be pointed out that the figures and the proportions represented in the figures are only schematic.

BRIEF DESCRIPTION OF THE DRAWINGS

The present disclosure will become more fully understood from the detailed description and the accompanying drawings, where.

Like reference symbols in the various drawings indicate like elements.

DETAILED DESCRIPTION

The following description is merely exemplary in nature and is in no way intended to limit the disclosure, its application, or uses.

Figure 1:
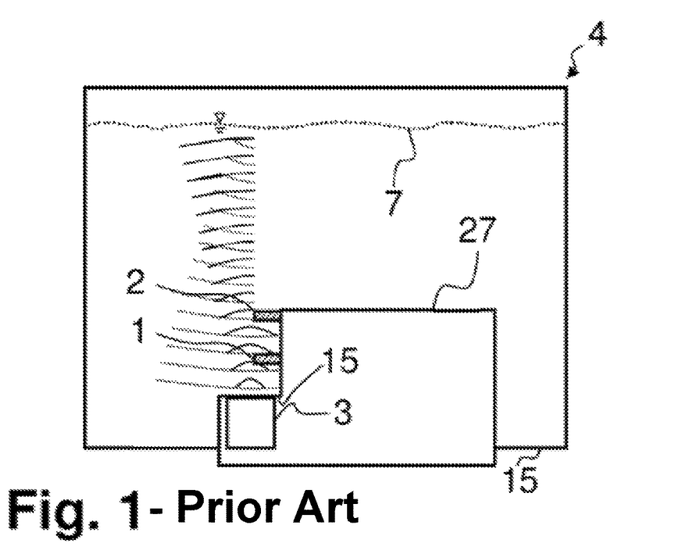
FIG. 1 is a schematic view of a tank with an exemplary ultrasonic level sensor.

FIG. 1 shows a tank 4 having an extraction unit 27 integrated in the tank wall 15 of the tank 4 in the region of a bottom of the tank. Liquid can be removed from the tank 4 with the extraction unit 27 and, for examples, an exhaust treatment device (not shown here) can be provided. The housing of the extraction unit 27 forms at least segments of the tank wall 15. An ultrasonic level sensor 3 is disposed in the extraction unit 27. There are a first reference surface 1 and a second reference surface 2 above the ultrasonic level sensor 3. The liquid in the tank forms a liquid level 7 up to which the liquid in the tank 4 extends (upwards).

Figures 2, 3:
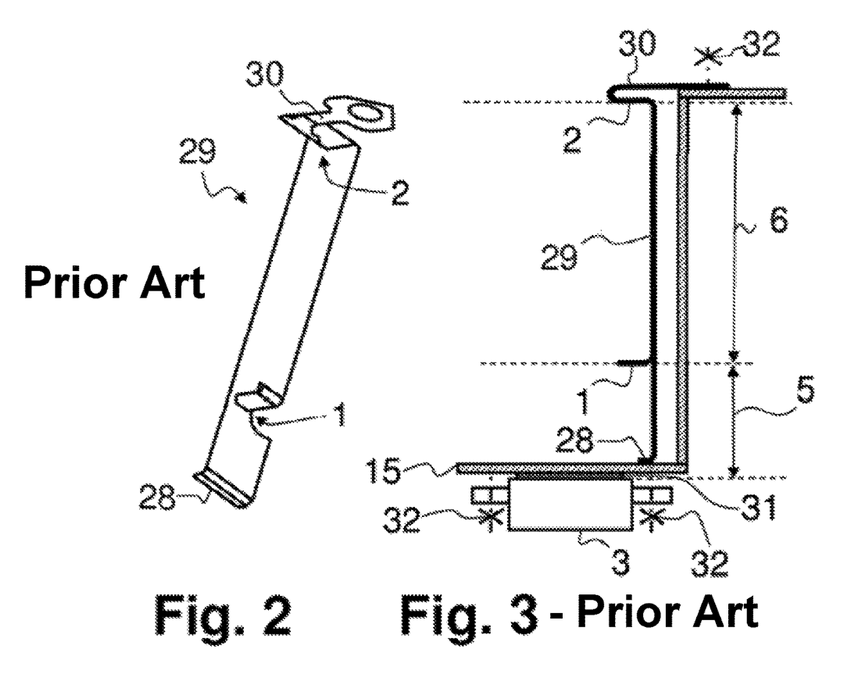
FIG. 2 is a schematic view of an exemplary component for providing reference surfaces.
FIG. 3 is a schematic view of an arrangement of an exemplary component with reference surfaces on an ultrasonic level sensor.

FIG. 2 shows a calibration component 29, which can be integrated within the tank 4 for providing the first reference surface 1 and the second reference surface 2. In some examples, the calibration component 29 consists of metal and can be produced with accurate maintenance of tolerances for the distances and positions of the first reference surface 1 and the second reference surface 2. In some examples, the calibration component 29 has a contact surface 28, which can rest (on the tank wall 15) near the ultrasonic level sensor 3 and hence determines the precise positioning of the calibration component 29. Moreover, the calibration component 29 may have a spring segment 30, which ensures that the calibration component 29 contacts the contact surface 28 precisely at a specified position on the tank wall 15. The position and orientation of the first reference surface 1 and the second reference surface 2 are accurately specified relative to the ultrasonic level sensor 3 in this way.

In FIG. 3 it can be seen how the calibration component 29 can be disposed on a tank wall 15 of the tank 4. In some examples, the calibration component 29 is fixed to the tank wall 15 by at least one screw 32. The contact surface 28 of the calibration component 29 is pressed fixedly on a specified point of the tank wall 15 by the spring segment 30. The ultrasonic level sensor 3 is disposed opposite the calibration component 29 on the tank wall 15 and is also fixed here, by way of example, by at least one screw 32. A first measuring distance 5 from the ultrasonic level sensor 3 to the first reference surface 1 and a second measuring distance 6 from the second reference surface 2 to the first reference surface 1 are defined by the positioning of the ultrasonic level sensor 3 and of the calibration component 29.

Figure 4:
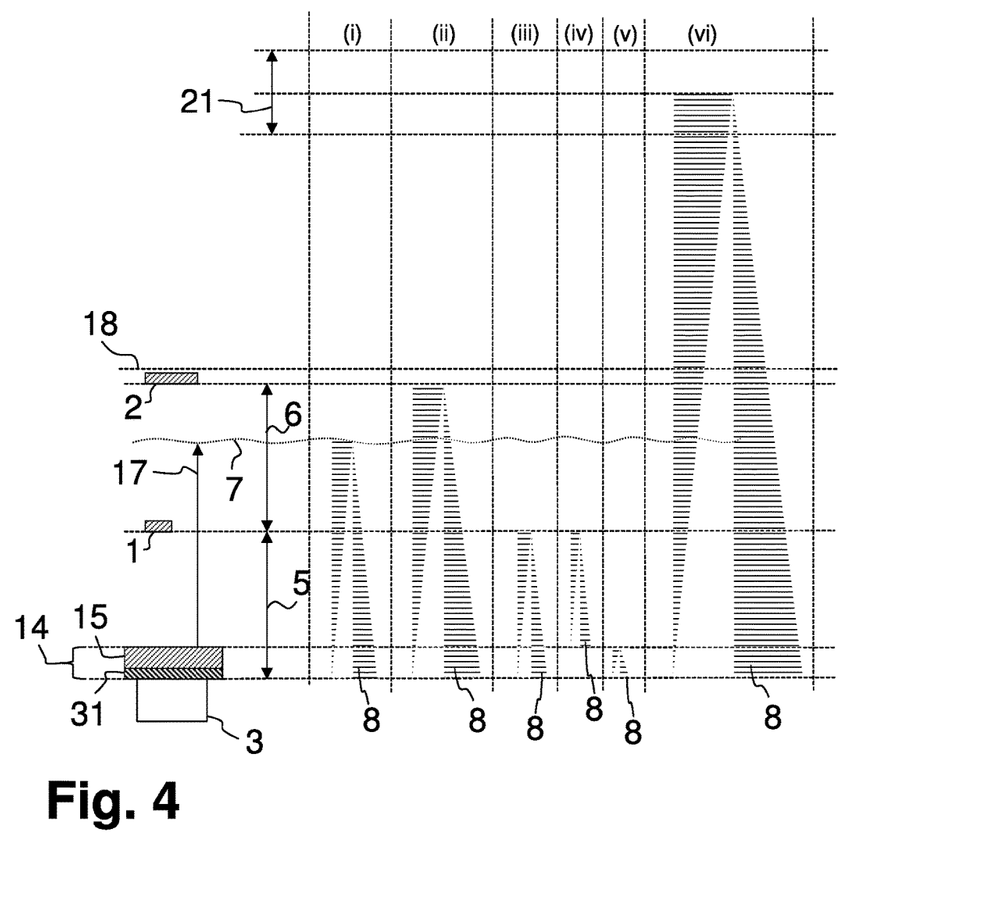
FIG. 4 is a diagram of the ultrasonic waves transmitted by an exemplary ultrasonic level sensor and their reflections.

FIG. 4 illustrates various propagation times 8 of ultrasonic waves or response signals that are emitted by the ultrasonic level sensor 3 and that are reflected by structures in the tank (e.g. by the first reference surface 1 or by the second reference surface 2). For better understanding, FIG. 4 partly shows structural features (e.g., the ultrasonic level sensor 3) and is partly in the form of a diagram. FIG. 4 shows an ultrasonic level sensor 3 at bottom left. Moreover, in FIG. 4 the tank wall 15, the first reference surface 1, the second reference surface 2 and a transmission means 31 that transmits ultrasonic waves from the ultrasonic level sensor 3 to the tank wall 15 are to be seen. The transmission means 31 can be, for example, a transfer paste or a transfer pad and together with the tank wall 15 forms a coupling layer 14, through which ultrasonic waves are introduced from the ultrasonic level sensor 3 into the tank (not shown here). A first measuring distance 5 is defined from the ultrasonic level sensor 3 to the first reference surface 1. A second measuring distance 6 is defined from the first reference surface 1 to the second reference surface 2. Moreover, another liquid level 7 in the tank (not shown here) and the level 17 in the tank arising therefrom are illustrated in FIG. 4. (i) characterizes a propagation time 8 of an ultrasonic wave from the ultrasonic level sensor 3 to the liquid level 7 and back to the ultrasonic level sensor 3. (ii) shows a propagation time 8 resulting from a reflection of ultrasonic waves at the second reference surface 2. (iii) shows a propagation time 8 resulting from the first reference surface 1. The propagation time 8 characterized by (iii) can be divided into a propagation time (iv) and a propagation time (v). the two propagation times 8 together give the propagation time 8 according to (iii). (v) thereby characterizes the propagation time 8 through the coupling layer 14 and (iv) the propagation time 8 through the liquid from the tank wall 15 up to the first reference surface 1. (vi) characterizes an (imaginary) propagation time 8 from the ultrasonic level sensor 3 to an (imaginary) liquid level, which is located at twice the height of the second reference surface 2. The propagation time 8 characterized by (vi) normally results not from a liquid level at the height but from a double reflection of ultrasonic waves at the liquid level and at the bottom of the tank. (vi) thus illustrates an imaginary, not actually existing state, which is identified with an incorrect interpretation of the response signals received by the ultrasonic level sensor. A time interval 21 is defined in the region of the propagation time 8 characterized by (vi), wherein the propagation times 8 lying in the region of the time interval 21 are taken into account in the context of the third selection criterion in order to decide whether a change back to the second propagation speed should take place.

Figure 5:
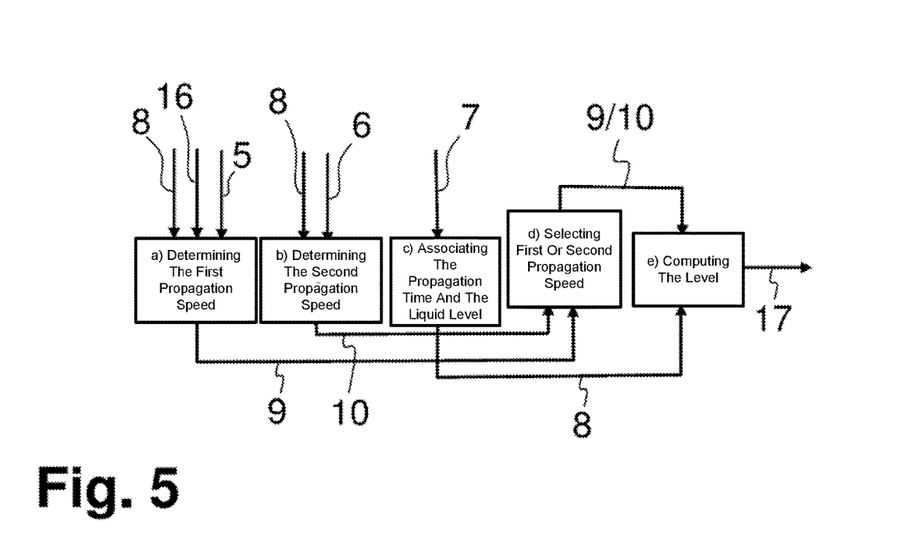
FIG. 5 is an exemplary flowchart of the described method.

FIG. 5 shows a flowchart of the described method. The steps a), b), c), d) and e) of the method can be seen. In step a) of the method, the propagation time 8 to the first reference surface, the described correction factor 16 for the coupling layer and the first measuring distance 5 are taken into account for determining the first propagation speed 9. Of course, other parameters and/or signals can also be taken into account here. In step b) the corresponding propagation time 8 and the second measuring distance 6 are taken into account for determining the second propagation speed 10.

Here too, taking other parameters into account is possible. In step c) the propagation time 8 to be associated with the liquid level 7 is determined. In step d) a selection of the first propagation speed 9 or the second propagation speed 10 takes place. The selected propagation speed 9/10 is used in step e), together with the propagation time 8 to the liquid level 7, to compute the level 17.

Figure 6:
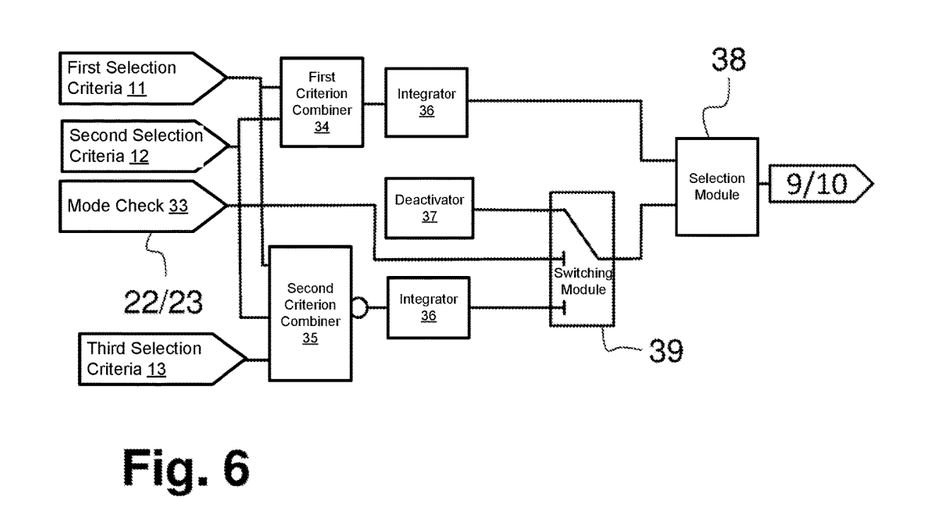
FIG. 6 is a schematic view of an exemplary logical circuit diagram of the described method.

FIG. 6 shows a logical circuit diagram, which illustrates the combination of the individual selection criteria 11, 12 and 13 for selection of the first propagation speed 9 or the second propagation speed 10. The selection of the propagation speed 9, 10 takes place in the selection module 38. For selection of the first propagation speed 9 it is necessary that both the first selection criterion 11 and also the second selection criterion 12 indicate a corresponding selection. For this the two selection criteria 11, 12 are combined with each other in a first criterion combiner 34 using an AND operation. The output of the first criterion combiner 34 is then filtered with an integrator 36. It is ensured by means of an integrator 36 that the first criterion combiner 34 specifies a change to the first propagation speed 9 for a specified minimum time interval before the selection module 38 makes a corresponding specification. For selection of the second propagation speed 10 it is necessary that the first selection criterion 11 and the second selection criterion 12 as well as an additional third selection criterion 13 specify selection of the second propagation speed 10. For this the three selection criteria 11, 12 and 13 are fulfilled together in a second criterion combiner 35 in the manner of a NAND operation. The NAND operation indicates that none of the three selection criteria 11, 12, 13 may specify the selection of the first propagation speed 9, thus the second propagation speed 10 is selected. The output of the second criterion combiner 35 is also filtered with an integrator 36 in order to ensure that the selection of the second propagation speed 10 is specified at least for a minimum time interval. The output of the second criterion combiner 35 additionally passes through a switching module 39 before it passes to the selection module 38. The selection of the second propagation speed 10 can be prevented by the switching module 39 if a mode check 33 determines a dynamic mode 23. The switching module 39 only enables the selection of the second propagation speed 10 if a stationary mode 22 exists. Otherwise, the corresponding input of the selection module 38 is connected to a deactivation means 37.

Figure 7:
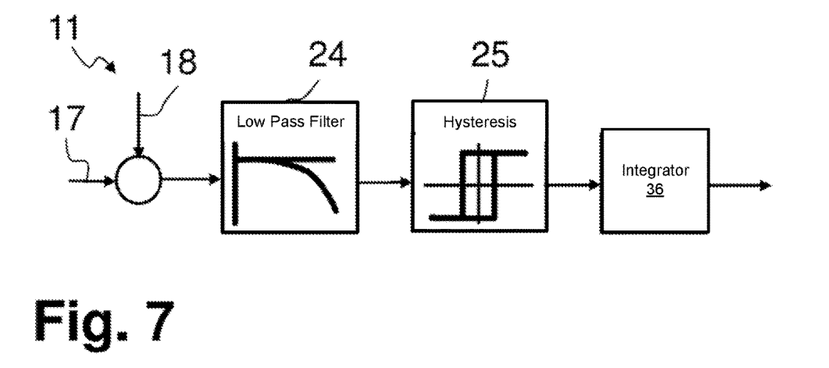
FIG. 7 is a schematic view of an exemplary first selection criterion.

FIG. 7 shows a flowchart of the first selection criterion 11. It can be seen that a level 17 is used as the input signal. The level 17 is filtered with a low pass filter 24 and a hysteresis 25 and is then processed by an integrator 36. It can be ensured by the integrator 36 that the first selection criterion has to be fulfilled for a specified period of time in order to cause a changeover between the propagation speeds in step d). The filtered input signal for the level is then compared with a level limit value.

Figure 8:
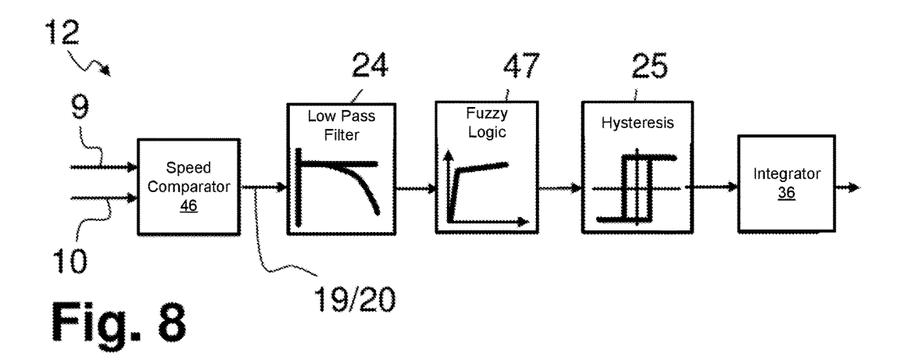
FIG. 8 is a schematic view of an exemplary second selection criterion.

In FIG. 8 the second selection criterion 12 can be seen. Here the first propagation speed 9 and the second propagation speed 10 are compared with a speed comparator 46. The resulting signal is first filtered by a low pass filter 24. Then a fuzzy logic 47 is applied to the signal. Small, permanently occurring deviations between the speeds are amplified by the fuzzy logic 47. The fuzzy logic 47 thus improves the identification of speed deviations caused by a reduction of the liquid level. Following the fuzzy logic 47 a hysteresis 25 is applied to the signal. Then the use of an integrator 36 takes place in order to only detect deviations between the first propagation speed 9 and the second propagation speed 10 occurring over long periods of time.

Figure 9:
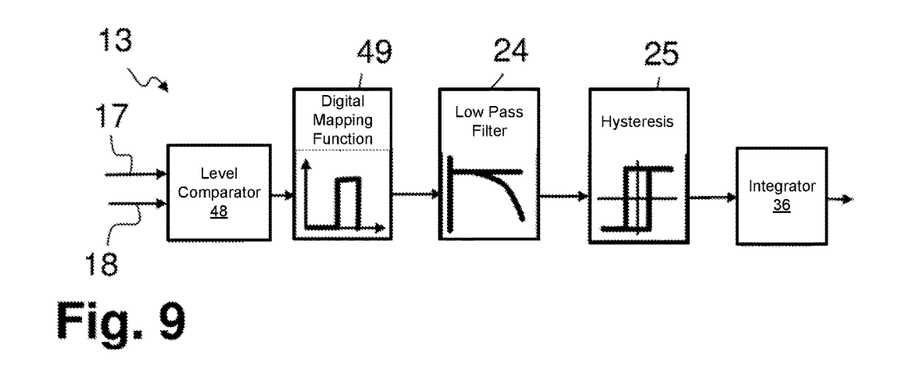
FIG. 9 is a schematic view of an exemplary third selection criterion.

FIG. 9 shows the third selection criterion of the described method. The level 17 is an input of the selection criterion. The level 17 is first compared with the level 18 corresponding to the second reference surface 2 in a level comparator 48. Then a digital mapping function 49 is used, with which it can be determined whether the level 17 corresponds accordingly to twice the height of the second reference surface 2. A low pass filter 24 and a hysteresis 25 as well as an integrator 36 are applied to the output signal of the digital mapping function 49.

Figure 10A:
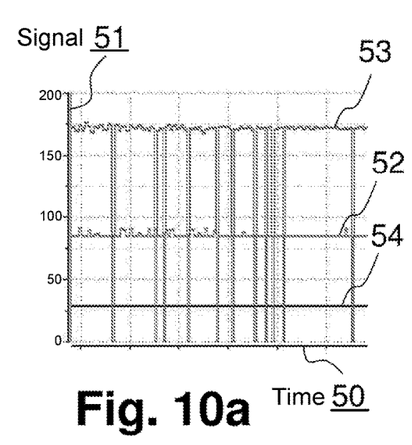
FIGS. 10a-10d are graphs of exemplary response signals at the ultrasonic level sensor under different conditions.
Figure 10B:
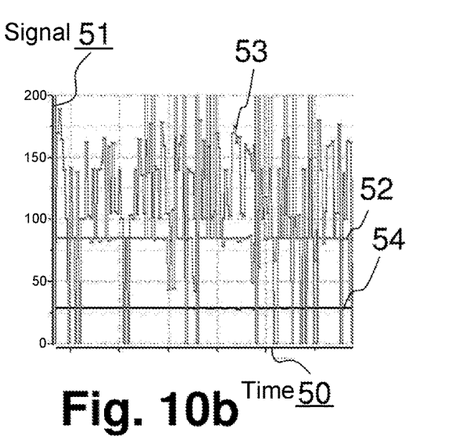

FIG. 10a to FIG. 10d explain the problem which occurs if the level in the tank 4 corresponds exactly to the height of the second reference surface 2 or to twice the height of the second reference surface 2. It may not be possible for the ultrasonic level sensor 3 to draw a distinction between these two levels under certain conditions. However, it is possible to draw a distinction between the two levels by specific analysis of the response signals at the ultrasonic level sensor 3. FIG. 10a and FIG. 10b each show a first response signal 54, a second response signal 52 and a third response signal 53 on the signal axis 51 with respect to a time axis 50. It has already been explained further above that the first response signal 54 is usually intended to be associated with the first reference surface 1, while the second response signal 52 is associated with the second reference surface 2, and the third response signal 53 is associated with the liquid surface 7 in the tank 4, with the liquid surface corresponding to the level.

FIG. 10a and FIG. 10b each show the response signals 54, 52, 53 that are produced if the level is exactly at the height of the second reference surface 2. FIG. 10a shows static conditions (also called the static mode further above) which are produced if the motor vehicle is at an absolute standstill and no vibrations and/or sloshing movements of the liquid in the tank occur. FIG. 10b shows dynamic conditions (also called the dynamic mode further above) which are produced if the motor vehicle is moving and vibrations and/or sloshing movements occur in the tank 4. The figures show that the first response signal 54 relating to the first reference surface 1 is constant both in FIG. 10a given static conditions and also in FIG. 10b given dynamic conditions, and also exhibits only minimum fluctuations, if at all, given dynamic conditions. This is because the first reference surface 1 is always below the level, independently of the dynamic mode. However, the second response signal 52 and the third response signal 53 differ between the dynamic mode and the static mode. In the static mode (FIG. 10a), the second response signal 52 is substantially constant, and the third response signal 53 exhibits only a few brief deviations. It has already been explained further above that the third response signal 53 is produced by a double reflection of the ultrasonic waves at the liquid level and at the bottom of the tank if the level corresponds to the height of the second reference surface 2. The liquid level is also briefly above the second reference surface 2 even in the event of minimal vibrations and/or sloshing movements in the tank.

In this case, the simple reflection of the ultrasonic waves at the liquid level is interpreted as a third response signal 53, and the third response signal 53 briefly falls. However, this effect does not reliably occur in the stationary mode because it cannot be assumed that minimal vibrations and/or sloshing movements occur in a reliable and uniform manner. Vibrations and/or sloshing movements regularly occur in the dynamic mode (FIG. 10b). As a result, the liquid level is regularly located above and below the second reference surface. This has the effect that both the second response signal 52 and the third response signal 53 are subject to severe fluctuations.

Figure 10C:
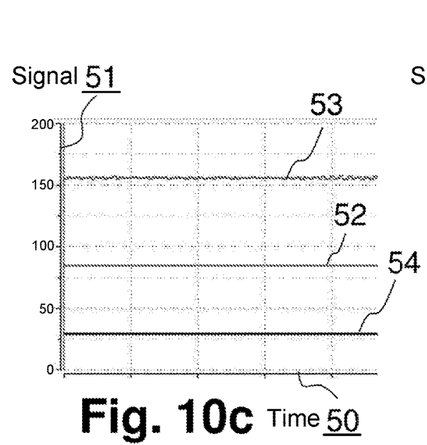
Figure 10D:
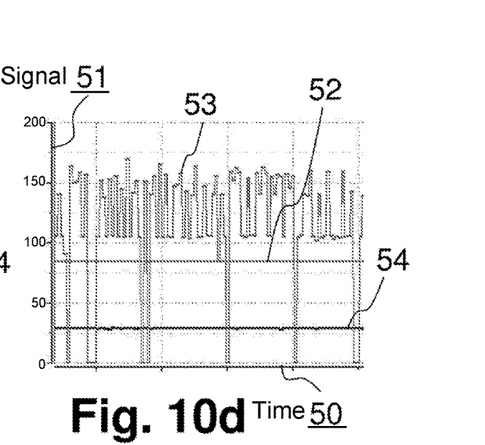

FIG. 10c and FIG. 10d each show the response signals 54, 52, 53 which are produced if the filling level is exactly twice the height of the second reference surface 2. In this case, FIG. 10c shows, in accordance with FIG. 10a, static conditions, while FIG. 10d, in accordance with FIG. 10b, shows dynamic conditions. The figures show that no fluctuations in the second response signal 52 occur under static conditions or under dynamic conditions. This is because the second reference surface is always below the level, independently of vibrations and sloshing movements. Fluctuations in the third response signal (53) regularly occur given dynamic conditions (FIG. 10d).

In this respect, it is possible to distinguish between whether the level corresponds to twice the height of the second reference surface 2 and whether the level corresponds to the height of the second reference surface by evaluating the second response signal 52 with respect to time. If there are fluctuations in the second response signal when the second response signal 52 is evaluated with respect to time, the level corresponds to the height of the second reference surface 2 and the third response signal 53 must not be evaluated as information relating to the level. If there are no fluctuations in the second response signal 52 when the response signal is evaluated with respect to time, the third response signal 53 corresponds to the actual level and can be accordingly evaluated.

Figure 11:
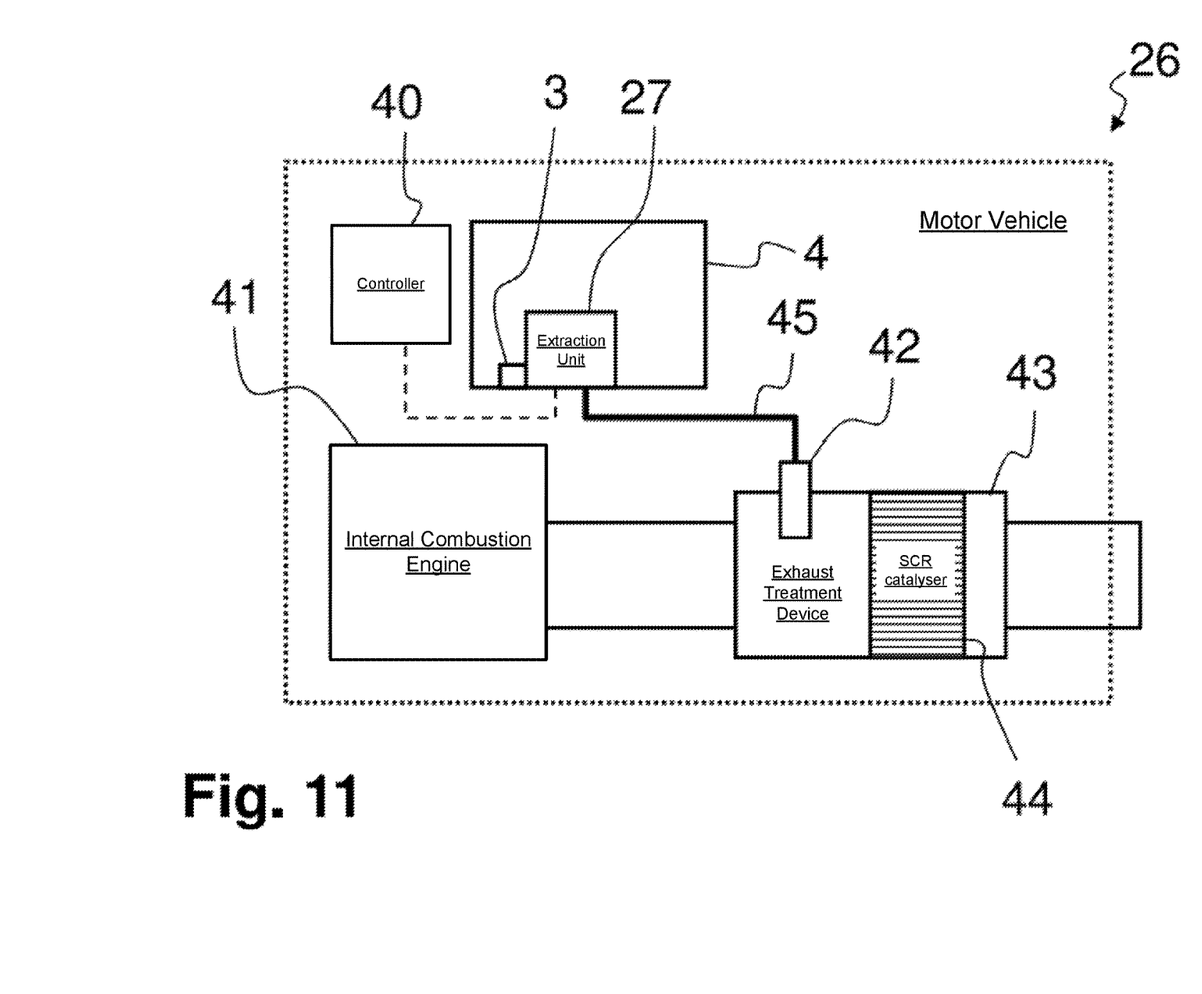
FIG. 11 is a schematic view of an exemplary motor vehicle having a tank and an ultrasonic level sensor, which can be operated according to the described method.

FIG. 11 shows a motor vehicle 26 including an internal combustion engine 41 and an exhaust treatment device 43 for cleaning the exhaust gases of the internal combustion engine 41. An SCR catalyser 44, with which the exhaust gases of the internal combustion engine 41 can be cleaned using the method of selective catalytic reduction, is disposed in the exhaust treatment device 43. For this, a liquid additive for exhaust gas cleaning can be delivered to the exhaust treatment device 43 by means of an injector 42. The liquid additive for exhaust gas cleaning is provided from a tank 4 via a line 45 from an extraction unit 27. The extraction unit 27 includes an ultrasonic level sensor 3, which is arranged to carry out the described method. The corresponding method is stored in a controller 40.

The description of the disclosure is merely exemplary in nature and, thus, variations that do not depart from the gist of the disclosure are intended to be within the scope of the disclosure. Such variations are not to be regarded as a departure from the spirit and scope of the disclosure.

What is claimed is:

1. A method for determining a level of a liquid in a tank, the method comprising:
 providing a tank supporting a liquid, the tank defining a tank wall;
 providing an ultrasonic level sensor supported by the tank, the ultrasonic level sensor having a transmitter unit and a receiver unit;
 emitting, from the transmitter unit an ultrasonic wave;
 receiving, at the receiver unit the emitted ultrasonic wave;
 providing a calibration component, the calibration component comprising:
  a spring segment;
  a contact surface pressed fixedly on the tank wall by way of the spring segment; and
  at least two reference surfaces for reflection of the ultrasonic wave, a first reference surface is disposed below a second reference surface;
 providing a controller in communication with the ultrasonic level sensor;
 a) determining, at the controller, a first propagation speed of an ultrasonic wave in the liquid over a first measuring distance from the ultrasonic level sensor to the first reference surface;
 b) determining, at the controller, a second propagation speed of an ultrasonic wave in the liquid over a second measuring distance from the first reference surface to the second reference surface;
 c) measuring, at the controller, a propagation time of an ultrasonic wave from the ultrasonic level sensor to a liquid level of the liquid in the tank;
 d) selecting, at the controller, the first propagation speed or the second propagation speed depending on a first selection criterion and checking, at the controller, the measured propagation speed as a second selection criterion, wherein the second propagation speed is not selected if the measured propagation time lies outside a time interval corresponding to twice the propagation time to the second reference surface and the first propagation speed was selected for a previous iteration of the method; and
 e) computing, at the controller, the level of the liquid with the propagation time measured in step c) and the propagation speed selected in step d).

2. The method of claim 1, wherein the ultrasonic level sensor is disposed outside of the tank and an ultrasonic wave of the ultrasonic level sensor passes through a coupling layer before it enters the liquid in the tank, wherein the coupling layer comprises a tank wall and the propagation time of the ultrasonic wave in the coupling layer is taken into account in step a) with a correction factor.

3. The method of claim 1, wherein steps a) through e) are repeated iteratively and when selecting the propagation speed in step d) a propagation speed selected for a previous iteration of the method is considered.

4. The method of claim 1, wherein a computed level is used as a first selection criterion in step e), wherein for a level below a level limit value the first propagation speed is selected and for a level above a level limit value the second propagation speed is selected.

5. The method of claim 1, wherein a comparison between the first propagation speed and the second propagation speed is performed as a third selection criterion in step d), wherein the first propagation speed is selected if a speed deviation between the first propagation speed and the second propagation speed exceeds a speed limit.

6. The method of claim 1, wherein, during the calculation of the level in step e), the following substeps are executed:
 i) computing the level based on the selected propagation speed;
 ii) checking whether a level which is determined at the second propagation speed corresponds to twice a height of the second reference surface;
 iii) determining a fluctuation in a second response signal of the second reference surface at the ultrasonic level sensor in a time interval;
 iv) checking whether the fluctuation in the second response signal exceeds a prespecified limit value; and
 v) correcting the level which is computed in step i) to the height of the second reference surface when steps ii) and iv) are complete.

7. The method of claim 1, wherein in step d) a change from the first propagation speed to the second propagation speed only takes place if a stationary mode exists.

8. The method of claim 1, wherein an input signal of the at least one selection criterion used in step d) is filtered with a low pass filter.

9. The method of claim 1, wherein an input signal of the at least one selection criterion used in step d) is filtered with a hysteresis.

10. A motor vehicle comprising:
a tank supporting a liquid and defining a tank wall;
an ultrasonic level sensor supported by the tank, the ultrasonic level sensor comprising:
a transmitter unit emitting an ultrasonic wave, and
a receiver unit receiving the emitted ultrasonic wave;
a calibration component comprising:
a spring segment;
a contact surface pressed fixedly on the tank wall by way of the spring segment; and
at least two reference surfaces for reflection of the ultrasonic wave, the at least two reference surfaces include a first reference surface and a second reference surface, wherein the first reference surface is disposed below the second reference surface; and
a controller in communication with the ultrasonic level sensor, the controller determines the level of the liquid in the tank by executing the following steps:
a) determining a first propagation speed of an ultrasonic wave in the liquid over a first measuring distance from the ultrasonic level sensor to the first reference surface;
b) determining a second propagation speed of the ultrasonic wave in the liquid over a second measuring distance from the first reference surface to the second reference surface;
c) measuring a propagation time of the ultrasonic wave from the ultrasonic level sensor to a liquid level of the liquid in the tank;
d) selecting the first propagation speed or the second propagation speed depending on a first selection criterion, and checking the measured propagation speed as a second selection criterion, wherein the second propagation speed is not selected if the measured propagation time lies outside a time interval corresponding to twice the propagation time to the second reference surface and the first propagation speed was selected for a previous iteration of the method; and
e) computing a level of the liquid with the propagation time measured in step c) and the propagation speed selected in step d).

11. The motor vehicle of claim 10, wherein the ultrasonic level sensor is disposed outside of the tank and an ultrasonic wave of the ultrasonic level sensor passes through a coupling layer before it enters the liquid in the tank, wherein the coupling layer comprises a tank wall and the propagation time of the ultrasonic wave in the coupling layer is taken into account in step a) with a correction factor.

12. The motor vehicle of claim 10, wherein steps a) through e) are repeated iteratively and when selecting the propagation speed in step d) a propagation speed selected for a previous iteration of the method is considered.

13. The motor vehicle of claim 10, wherein a computed level is used as a first selection criterion in step e), wherein for a level below a level limit value the first propagation speed is selected and for a level above a level limit value the second propagation speed is selected.

14. The motor vehicle of claim 10, wherein a comparison between the first propagation speed and the second propagation speed is performed as a third selection criterion in step d), wherein the first propagation speed is selected if a speed deviation between the first propagation speed and the second propagation speed exceeds a speed limit.

15. The motor vehicle of claim 10, wherein, during the calculation of the level in step e), the following substeps are executed:
i) computing the level based on the selected propagation speed;
ii) checking whether a level which is determined at the second propagation speed corresponds to twice a height of the second reference surface;
iii) determining a fluctuation in a second response signal of the second reference surface at the ultrasonic level sensor in a time interval;
iv) checking whether the fluctuation in the second response signal exceeds a prespecified limit value; and
v) correcting the level which is computed in step i) to the height of the second reference surface when steps ii) and iv) are complete.

16. The motor vehicle of claim 10, wherein in step d) a change from the first propagation speed to the second propagation speed only takes place if a stationary mode exists.

17. The motor vehicle of claim 10, wherein an input signal of the at least one selection criterion used in step d) is filtered with a low pass filter.

18. The motor vehicle of claim 10, wherein an input signal of the at least one selection criterion used in step d) is filtered with a hysteresis.

19. A method for determining a level of a liquid in a tank, the method comprising:
providing a tank supporting a liquid, the tank defining a tank wall;
providing an ultrasonic level sensor supported by the tank, the ultrasonic level sensor having a transmitter unit and a receiver unit;
emitting, from the transmitter unit an ultrasonic wave;
receiving, at the receiver unit the emitted ultrasonic wave;
providing a calibration component, the calibration component comprising:
a spring segment;
a contact surface pressed fixedly on the tank wall by way of the spring segment; and
at least two reference surfaces for reflection of the ultrasonic wave, a first reference surface is disposed below a second reference surface;
providing a controller in communication with the ultrasonic level sensor;
a) determining, at the controller, a first propagation speed of an ultrasonic wave in the liquid over a first measuring distance from the ultrasonic level sensor to the first reference surface;
b) determining, at the controller, a second propagation speed of an ultrasonic wave in the liquid over a second measuring distance from the first reference surface to the second reference surface;
c) measuring, at the controller, a propagation time of an ultrasonic wave from the ultrasonic level sensor to a liquid level of the liquid in the tank;
d) selecting, at the controller, the first propagation speed or the second propagation speed depending on a first selection criterion; and
e) computing, at the controller, a level with the propagation time measured in step c) and the propagation speed selected in step d) by executing the following substeps:
i) computing the level based on the selected propagation speed;
ii) checking whether a level which is determined at the second propagation speed corresponds to twice a height of the second reference surface;

iii) determining a fluctuation in a second response signal of the second reference surface at the ultrasonic level sensor in a time interval;

iv) checking whether the fluctuation in the second response signal exceeds a prespecified limit value; and v) correcting the level which is computed in step i) to the height of the second reference surface when steps ii) and iv) are complete.

20. A motor vehicle comprising:

a tank supporting a liquid and defining a tank wall;

an ultrasonic level sensor supported by the tank, the ultrasonic level sensor comprising:
   a transmitter unit emitting an ultrasonic wave, and
   a receiver unit receiving the emitted ultrasonic wave;

a calibration component comprising:
   a spring segment;
   a contact surface pressed fixedly on the tank wall by way of the spring segment; and
   at least two reference surfaces for reflection of the ultrasonic wave, the at least two reference surfaces include a first reference surface and a second reference surface, wherein the first reference surface is disposed below the second reference surface; and a controller in communication with the ultrasonic level sensor, the controller determines the level of the liquid in the tank by executing the following steps:

a) determining a first propagation speed of an ultrasonic wave in the liquid over a first measuring distance from the ultrasonic level sensor to the first reference surface;

b) determining a second propagation speed of the ultrasonic wave in the liquid over a second measuring distance from the first reference surface to the second reference surface;

c) measuring a propagation time of the ultrasonic wave from the ultrasonic level sensor to a liquid level of the liquid in the tank;

d) selecting the first propagation speed or the second propagation speed depending on at least one selection criterion; and e) computing a level with the propagation time measured in step c) and the propagation speed selected in step d) by executing the following subsets:

i) computing the level based on the selected propagation speed;

ii) checking whether a level which is determined at the second propagation speed corresponds to twice a height of the second reference surface;

iii) determining a fluctuation in a second response signal of the second reference surface at the ultrasonic level sensor in a time interval;

iv) checking whether the fluctuation in the second response signal exceeds a prespecified limit value; and v) correcting the level which is computed in step i) to the height of the second reference surface when steps ii) and iv) are complete.

* * * * *